United States Patent
Tsay et al.

(10) Patent No.: US 6,545,176 B1
(45) Date of Patent: Apr. 8, 2003

(54) APPARATUS AND PROCESS FOR THE HIGH YIELD PRODUCTION OF METHYL METHACRYLATE OR METHACRYLIC ACID

(75) Inventors: Chorng-Shyuan Tsay, Maple Glen, PA (US); Makarand Dattatraya Phadke, Pune (IN); Abraham Benderly, Houston, TX (US); I-Hwa Midey Chang-Mateu, Ambler, PA (US); Nicole Rendon Koegel, Houston, TX (US); Heather Granzin Thompson, Missouri City, TX (US); Diana Elaine Chase, League City, TX (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/428,729

(22) Filed: Oct. 28, 1999

Related U.S. Application Data

(60) Provisional application No. 60/106,947, filed on Nov. 4, 1998.

(51) Int. Cl.[7] ................................................ C07C 67/22
(52) U.S. Cl. ...................... 560/215; 560/179; 560/187
(58) Field of Search ................................ 560/215, 179, 560/187

(56) References Cited

U.S. PATENT DOCUMENTS

| | | | | |
|---|---|---|---|---|
| 2,373,464 A | * | 4/1945 | Dittmar | 560/215 |
| 2,416,756 A | * | 3/1947 | Jilk | 560/251 |
| 2,786,739 A | * | 3/1957 | Eck et al. | 423/549 |
| 3,027,328 A | * | 3/1962 | Huter | 558/351 |
| 3,974,207 A | * | 8/1976 | Szelejewski et al. | 560/212 |
| 4,464,539 A | | 8/1984 | Hashimoto et al. | |
| 4,529,816 A | | 7/1985 | DeColibus et al. | 560/212 |
| 4,748,268 A | | 5/1988 | Pietsch et al. | 560/205 |
| 5,087,736 A | * | 2/1992 | Higuchi et al. | 560/215 |
| 5,393,918 A | | 2/1995 | Dobson | 560/215 |

FOREIGN PATENT DOCUMENTS

| | | |
|---|---|---|
| EP | 0 202 099 A2 | 11/1986 |
| EP | 0 686 623 A1 | 12/1995 |

* cited by examiner

*Primary Examiner*—Alan L. Rotman
*Assistant Examiner*—Taylor V. Oh
(74) *Attorney, Agent, or Firm*—Alan Holler

(57) ABSTRACT

A high yield process for the production of methyl methacrylate or methacrylic acid and an apparatus for increasing the yield in a process for the production of methyl methacrylate or methacrylic acid are disclosed.

15 Claims, 2 Drawing Sheets

APPARATUS AND PROCESS FOR THE HIGH YIELD PRODUCTION OF METHYL METHACRYLATE OR METHACRYLIC ACID

This is a nonprovisional application of prior pending provisional application Ser. No. 60/106,947 filed Nov. 4,1998.

This invention relates to a high yield process for the production of methyl methacrylate ("MNA") or methacrylic acid ("MAA") and an apparatus for increasing the yield in a process for the production of MMA or MAA.

A number of commercial processes are used to prepare MMA. In one such process, MMA is prepared from acetone cyanohydrin ("ACH"). The process is described in U.S. Pat. No. 4,529,816 ("816"). In this process, ACH is (1) hydrolyzed by sulfuric acid to produce α-hydroxyisobutyramide ("HIBAM") and its sulfate ester, α-sulfatoisobutyramide ("SIBAM"); (2) the HIBAM and SIBAM are thermally converted to 2-methacrylamide ("MAM") and a small amount of methacrylic acid ("MAA"); which are then (3) esterified with methanol to produce MMA. Residual HIBAM is esterified to methyl α-hydroxyisobutyrate ("MOB"). In step (2) of the reaction, the conversion of SIBAM to MAM occurs more readily than the conversion of HIBAM to MAM. In order to facilitate the thermal conversion of HIBAM to MAM, both heat and increased residence time must be provided. A decrease in thermal conversion to desired products results in a decreased overall yield for the process. The process of preparing MAA can be the same as that used to prepare MMA, except that instead of esterifying MAM and MAA with methanol, water is added to the MAM and MAA mixture to convert the MAM to MAA.

The MMA and MAA markets are extremely cost sensitive. A slight improvement in process yield can result in a significant market advantage. There is a need for an improved yield commercial process of preparing MMA or MAA.

One attempt to improve the yield of a MMA process is disclosed in U.S. Pat. No. 5,393,918. In addition to the conversion of MAM to MMA, the patent discloses a process whereby the HIBAM and SIBAM from step (1) above are esterified to methyl-α-methoxyisobutyrate ("α-MEMOB"), methyl-β-methoxyisobutyrate ("β-MEMOB"), and methyl α-hydroxyisobutyrate ("MOB"). The α-MEMOB, β-MEMOB, and MOB are later isolated and converted to MMA in a separate step. This eliminates the need for thermal conversion of HIBAM and SIBAM to MAM, but requires fractional distillation to separate out α-MEMOB, β-MEMOB, and MOB from MMA and a subsequent dehydration step to convert α-MEMOB, β-MEMOB, and MOB to MMA.

Figure 1:
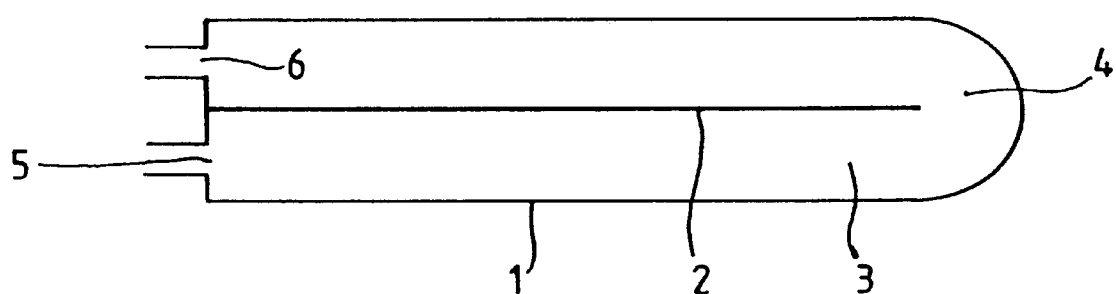

Thermal conversion of HIBAM and SIBAM to MAM typically is performed in a cracker reactor. The cracker reactor contains a heat exchanger to provide the heat necessary for the cracking reaction and a thermal conversion apparatus which provides the necessary retention time under the heated conditions for the cracking reaction to take place. A typical thermal conversion apparatus 1 of a cracker reactor known in the art is a multi-pass metal pipe (FIG. 1). In one embodiment, the metal pipe may contain a baffle 2 which separates the pipe to provide a passage 3 having a 180° turn 4 to minimize the space required to house the cracker reactor, an expansion 5 where the reactants enter the thermal conversion apparatus, and a constriction 6 where the cracker reactor mixture exits the thermal conversion apparatus. These features of a typical thermal conversion apparatus result in backmixing of the HIBAM, SIBAM, MAM, and MAA. Backmixing of these components results in less than plug flow and decreased overall yields because the retention time of the components in the cracker reactor will vary. Some of each component will have insufficient retention time in the cracker reactor, while another portion of each component may have an extended retention time in the cracker reactor. As a result of insufficient retention time in the cracker reactor, there may be an under conversion of HIBAM. As a result of an extended retention time in the cracker reactor, there may be an over conversion or degradation of SIBAM, MAM, and MAA.

U.S. Pat. No. 4,748,268 discloses a process for preparing methacrylic acid esters using a plug flow reactor. In the process, a feed stream containing methacrylic acid, a $C_1$–$C_4$ saturated aliphatic alcohol, a catalyst, and a liquid organic substance is continuously fed into a plug flow reactor. The plug flow reactor is utilized for the esterification reaction. The process does not address the conversion of HIBAM and SIBAM to MAM in a thermal conversion apparatus.

Despite the disclosure of the prior art, there is a continuing need for an improved yield commercial process of preparing MMA.

We have discovered that the use of plug flow in the thermal conversion apparatus of a MMA process significantly improves the thermal conversion of HIBAM and SIBAM to MAM, and therefore provides an improved overall process yield. By plug flow is meant that the velocity of the fluid in the pipe is nearly the same throughout the cross section of the pipe.

In a first aspect, the present invention provides a process for preparing a monomer selected from methacrylic acid and methyl methacrylate, including: (A) hydrolyzing acetone cyanohydrin to produce a hydrolysis mixture including α-hydroxyisobutyramide, α-sulfato isobutyramide, 2-methacrylamide, and methacrylic acid; (B) thermally converting the hydrolysis mixture in a cracker reactor including a plug flow thermal conversion apparatus with the necessary retention time to produce a cracker reactor mixture including 2-methacrylamide and methacrylic acid; (C) reacting the cracker reactor mixture and a material selected from methanol and water in at least one reactor to produce a monomer selected from methacrylic acid and methyl methacrylate.

In a second aspect, the present invention provides a thermal conversion apparatus, including: a pipe with means for maintaining plug flow.

In the process of the invention, ACH is hydrolyzed to produce a hydrolysis mixture including, but not limited to, MAM, MAA, HIBAM, and SIBAM. As is known in the art, the amount of each component in the hydrolysis mixture will vary depending on the reaction conditions. The hydrolysis reaction is run in an excess of sulfuric acid. The concentration of the sulfuric acid feed used is not critical, however a concentration of from 95% to 100% is preferred.

Any reactor known in the art, suitable for conducting hydrolysis reactions, may be utilized for the hydrolysis reaction. The hydrolysis may be conducted in one hydrolysis reactor. Alternatively, the hydrolysis may be conducted in more than one hydrolysis reactor. If more than one hydrolysis reactor is utilized, the hydrolysis reactors are generally connected in series. It is contemplated that a parallel arrangement of the hydrolysis reactors could be useful in certain instances. In one embodiment, from 1 to 5 reactors connected in series may be useful for conducting the hydrolysis reaction. It is preferred that a series of 2 or 3 reactors be used for the hydrolysis reaction.

The hydrolysis is typically conducted at a temperature ranging from 70° C. to 135° C., preferably 75° C. to 105° C.

The temperature can be maintained at one value or changed during the course of the hydrolysis reaction in each hydrolysis reactor utilized. If more than one reactor is used, preferably the temperature of the first reactor ranges from 75° C. to 90° C., the temperature of subsequent reactors ranges from 90° C. to 105° C. The hydrolysis is conducted for a time sufficient to maximize the pre-esterification yield of HIBAM, SIBAM, MAM, and MAA. The time required for hydrolysis may vary from 1 minute to 60 minutes, although longer times may be required.

The hydrolysis mixture is transferred to the cracker reactor including a plug flow thermal conversion apparatus and thermally converted to a cracker reactor mixture. The cracker reactor mixture includes, but is not limited to predominantly MAM and lesser amounts of MAA, HIBAM, and SIBAM.

The first part of the cracker reactor is a heating unit. The cracker reactor heating unit may be a pre-heater and a heater. The cracker reactor pre-heater and heater are typically heat exchangers. The cracker reactor pre-heater and heater are utilized to bring the reaction mixture up to the temperature necessary for the cracking reaction to occur. The exit temperature in the cracker reactor pre-heater typically ranges from 110° C. to 135° C. The exit temperature in the cracker reactor heater typically ranges from 135° C. to 165° C. Alternatively, the cracker reactor pre-heater and heater may be collapsed into one heating unit. If one cracker reactor heating unit is utilized, the exit temperature in the heating unit typically ranges from 135° C. to 165° C. Any type of heat exchanger known in the art will suffice as the cracker reactor pre-heater and heater, so long as it is resistant to the elevated temperatures and strongly acidic conditions present in this process. Suitable heat exchangers include plate and frame, plate and fin, spiral, and tubular. Suitable materials of construction include, but are not limited to Hastelloy B, Hastelloy B-2, Hastelloy B-3, Inconel, and tantalum alloys.

Figure 2:
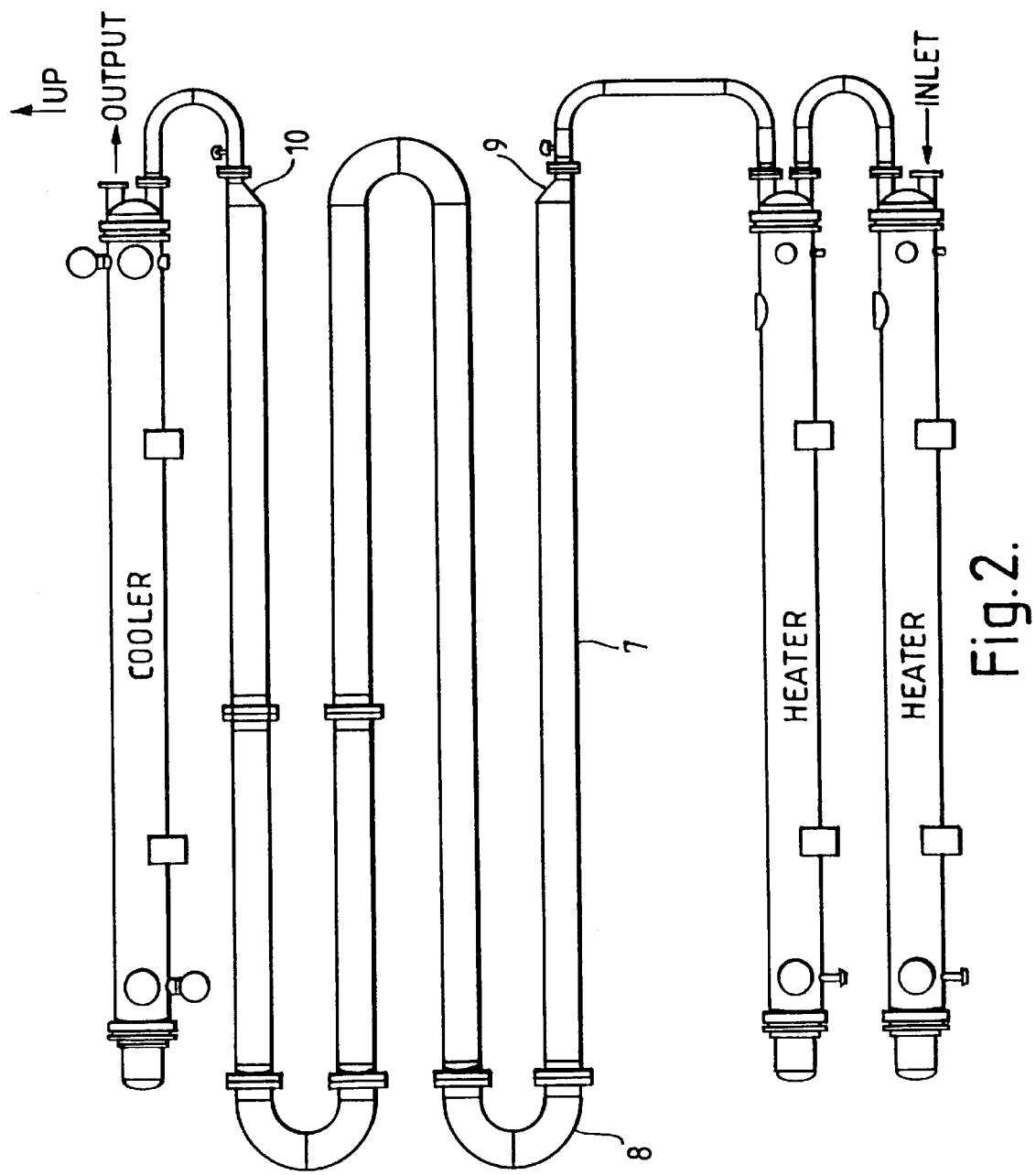

The second part of the cracker reactor is the thermal conversion apparatus of the invention (FIG. 2). As recited above, the thermal conversion apparatus is where the thermal conversion of the hydrolysis mixture, i.e., HIBAM and SIBAM, to MAM occurs. The critical aspect of the invention is control of the residence time of the reactants in the thermal conversion apparatus. The thermal conversion apparatus must provide the retention time required under suitable temperatures to complete the cracking reaction, without causing degradation of the desired products. It is understood that the desired retention time will vary depending on the hydrolysis mixture and the temperature in the thermal conversion apparatus. In general, the desired retention typically ranges from 1 to 15 minutes, preferably 2 to 12 minutes, more preferably 3 to 10 minutes, however as discussed above, longer retention times may be necessary based on the hydrolysis mixture and the temperature in the thermal conversion apparatus.

The control of retention time in the thermal conversion apparatus is provided by maintaining plug flow in the apparatus. Many embodiments are contemplated for design of the thermal conversion apparatus of the present invention which are suitable for maintaining plug flow and thus providing the desired retention time. In one embodiment, the thermal conversion apparatus is at least one straight pipe. In an alternative embodiment, where space limitations necessitate turns in the pipe, plug flow is maintained in the thermal conversion apparatus with the use of Cheng Rotation Vanes (CRV™-Trademark of Cheng Fluid Systems) or similar equipment in the turns of the at least one pipe. In another embodiment, plug flow is maintained by selecting the geometry of the apparatus, such as pipe diameters and lengths, the turns of the at least one pipe within the apparatus, and provision of gradual expansion at the entry and constriction at the exit from the apparatus. The gradual expansion and constriction may be concentric or eccentric, and may be provided by the use of LAD™ (large angle diffusers-Trademark of Cheng Fluid Systems) or similar equipment, or a specially designed at least one pipe. In this embodiment, the diameter of the at least one pipe of the thermal conversion apparatus is typically from 2 to 36 cm, preferably from 10 to 30 cm, more preferably from 15 to 28 cm. The length of the at least one pipe of the thermal conversion apparatus is sufficient to provide enough residence time for the hydrolysis mixture to be thermally converted to MAM. The turns of the at least one pipe are designed to be smooth in order to minimize backmixing.

The design of the thermal conversion apparatus described above is not intended to be limiting, as the design of the geometry of the thermal conversion apparatus to maintain plug flow is within the expertise of one skilled in the art. The factors to be considered in designing the thermal conversion apparatus include maintaining plug flow, the desired retention time, the flow rate, the reaction mixture, and the temperature within the thermal conversion apparatus.

The thermal conversion apparatus of one embodiment of this invention includes a pipe 7 having plug flow. The pipe may be made of any material which is resistant to strong acid and high temperature. Suitable materials include, but are not limited to Hastelloy B, Hastelloy B-2, Hastelloy B-3, and tantalum alloys. The length of the pipe of the thermal conversion apparatus is sufficient to provide the desired retention time.

Plug flow in the pipe of the thermal conversion apparatus may generally be maintained by at least one of six design features. Some of these features are illustrated in FIG. 2. The pipe of the thermal conversion apparatus may contain turns 8 which are smooth (see FIG. 2). The pipe of the thermal conversion apparatus may contain an expansion 9 at the beginning of the thermal conversion apparatus, wherein the expansion is gradual so as to minimize back mixing of reactants entering the pipe (see FIG. 2). The pipe of the thermal conversion apparatus may contain a constriction 10 at the end of the thermal conversion apparatus, wherein the constriction is gradual so as to minimize back mixing of material exiting the pipe (see FIG. 2). The diameter of the pipe may be selected so as to favor plug flow. The pipe may also be straight, in which case, plug flow is maintained. An alternative to having smooth turns in the pipe while maintaining plug flow is to have a CRV™ in each turn. Such a design, incorporating any of the features described above, reduces backmixing and maintains plug flow at this point in the process. As a result of the reduced back mixing, yield losses in the thermal conversion are reduced, therefore the overall process yield is increased. The thermal conversion typically is run at temperatures ranging from 135° C. to 165° C. The temperature may vary or be constant within this range.

The third part of the cracker reactor is the cracker reactor cooler. The cracker reactor cooler may be at least one heat exchanger which is used to lower the temperature of the cracker reactor mixture prior to the esterification reaction to prevent degradation of the cracker reactor mixture. The cracker reactor cooler may be any type of heat exchanger so long as it is resistant to the elevated temperatures and strongly acidic conditions present in this process. Suitable heat exchangers include plate and frame, plate and fin, spiral, and tubular. Suitable materials of construction include, but are not limited to Hastelloy B, Hastelloy B-2, Hastelloy B-3, and tantalum alloys. The exit temperature in the cracker reactor cooler typically ranges from 90° C. to 110° C.

The retention time in the cracker reactor including the cracker reactor pre-heater and heater, the thermal conversion apparatus, and the cracker reactor cooler may vary based on the reaction mixtures and temperatures, but is typically from 1 minute to 30 minutes, preferably 3 minutes to 20 minutes, more preferably 5 minutes to 15 minutes.

The cracker reactor mixture may be transferred to at least one reactor, wherein the cracker reactor mixture is either contacted with methanol and reacted by methods known in the art to produce an esterification mixture which includes, but is not limited to, predominantly MMA, with lesser amounts of MAA, MAM, MEMOB, MOB, methanol, mineral acids and MMA/MAA copolymer, or contacted with water and reacted by methods known in the art to produce a mixture which includes predominantly MAA. The reaction conditions are not critical and can be varied over a wide range. The only requirement is that the conditions be mild enough such that side reactions leading to degradation products do not occur to an unacceptable extent. The reaction is typically run at a temperature ranging from 85° C. to 180° C. The temperature can be maintained at one value or changed during the course of the reaction. The esterification reaction may be run in a continuous flow stirred tank reactor or a plug flow reactor as previously described. Alternatively, the esterification reaction may be run in one or more reactors. If more than one reactor is utilized, they may be connected in parallel or in series.

The MMA and MAA in the esterification reactor mixture are isolated from the esterification reactor mixture. Such isolation may be done by any method known in the art. For instance, the MMA and MAA from the esterification reaction are isolated by separation of the esterification mixture into organic and inorganic phases. Generally the organic phase will contain a major amount of MMA and a minor amount of MAA and the inorganic phase will contain predominantly sulfuric acid. The organic acid MAA may be isolated using an aqueous basic wash, such as an aqueous ammonia solution, sodium, calcium, or potassium hydroxide, calcium or sodium carbonate, or organic amines, such as trimethyl amine. The basic compound of the aqueous basic wash forms a salt with the MAA which is soluble in the aqueous phase, formed by addition of the aqueous basic wash, and less soluble in the organic phase. Accordingly, the MMA partitions towards the organic phase and the MAA salt partitions towards the aqueous phase. The aqueous basic wash may be added during separation of the esterification mixture into the organic and inorganic phases. In such case, a suitable amount of basic wash is added so that the inorganic acid phase is neutralized and the MAA salt formed. Alternatively, the organic phase may be removed and the basic wash added at some point thereafter.

Occasionally, a stable emulsion forms after the basic wash. In order to facilitate breaking the emulsion and separating the aqueous and organic phases formed during the basic aqueous wash, a low level of a strong acid or a strong acid salt may be added to the area where the separation is to occur. This strong acid or strong acid salt acts as a deemulsifier. Suitable strong acids or strong acid salts include, but are not limited to sulfuric acid, methane sulfonic acid, ammonium hydrogen sulfate, or p-toluene sulfonic acid. Sulfuric acid is preferred. The level of strong acid or strong acid salt added may range from 100 ppm to 5,000 ppm, preferably 200 ppm to 1,000 ppm.

The organic phase may then be removed and the MMA purified by methods known in the art, for instance, by various distillation techniques to provide suitable purity grades of MMA monomer as the end use requires. The MAA salt in the aqueous phase is generally re-acidified and the MAA recovered by known methods. The MAA then may be recycled for further use.

Polymerization inhibitors are useful to prevent polymerization both during the process of preparing MMA and during storage and shipment of MMA. The polymerization inhibitor may include a water soluble or alcohol soluble polymerization inhibitor. Suitable examples include but are not limited to, hydroquinone; 4-methoxyphenol; 4-ethoxyphenol; 4-propoxyphenol; 4-butoxyphenol; 4-heptoxyphenol; hydroquinone monobenzylether; 1,2-dihydroxybenzene; 2-methoxyphenol; 2,5-dichlorhydroquinone; 2,5-di-tert-butylhydroquinone; 2-acetylhydroquinone; hydroquinone monobenzoate; 1,4-dimercaptobenzene; 1,2-dimercaptobenzene; 2,3,5-trimethylhydroquinone; 4-aminophenol; 2-aminophenol; 2-N, N-dimethylaminophenol; 2-mercaptophenol; 4-mercaptophenol; catechol; monobutylether; 4-ethylaminophenol; 2,3-dihydroxyacetophenone; pyrogallol; 1,2-dimethylether; 2-methylthiophenol; t-butyl catechol; di-tert-butylnitroxide; di-tert-amylnitroxide; 2,2,6,6-tetramethyl-piperidinyloxy; 4-hydroxy-2,2,6,6-tetramethyl-piperidinyloxy; 4-oxo-2,2,6,6-tetramethyl-piperidinyloxy; 4-dimethylamino 2,2,6,6-tetramethyl-piperidinyloxy; 4-amino-2,2,6,6-tetramethyl-piperidinyloxy; 4-ethanoyloxy-2,2,6,6-tetramethyl-piperidinyloxy; 2,2,5,5-tetramethyl-pyrrolidinyloxy; 3-amino-2,2,5,5-tetramethyl-pyrrolidinyloxy; 2,2,5,5-tetramethyl- 1-oxa-3-azacyclopentyl-3-oxy; 2,2,5,5-tetramethyl-3-pyrrolinyl-1-oxy-3-carboxylic acid; 2,2,3,3,5,5,6,6-octamethyl- 1,4-diazacyclohexyl-1,4-dioxy; sodium nirosophenolate; copper compounds such as copper dimethyldithiocarbamate; copper diethyldithiocarbamate; copper dibutyldithiocarbamate; copper salicylate; methylene blue; iron; phenothiazine; 1,4-benzenediamine, N-(1,4-dimethylpentyl)-N'-phenyl; 1,4-benzenediamine, N-(1,3-dimethylbutyl)-N'-phenyl; isomers thereof; mixtures of two or more thereof; or mixtures of one or more of the above with molecular oxygen. The polymerization inhibitor is typically used at levels ranging from 100 ppm to 4,000 ppm by weight.

The process of this invention ultimately relies on the esterification of MAM to MMA. Therefore, the thermal conversion of HIBAM and SIBAM to MAM are critical to the process providing high yields. It is therefore possible to measure the efficiency of the process of the invention by measuring the yield after the hydrolysis reaction and the yield after the thermal conversion in the process of the invention and then subtracting the yield after the thermal conversion from the yield after the hydrolysis reaction. The yield after the hydrolosis reaction is the measured amounts of HIBAM, SIBAM, MAA, and MAM. The yield after the thermal conversion is the measured amounts of MAA and MAM. The following Examples are intended to illustrate the process and the thermal conversion apparatus of the invention.

For Examples 1–10 (Comparative), the process of the invention was run utilizing the thermal conversion apparatus of FIG. 1. ACH was hydrolyzed to HIBAM; SIBAM, MAM, and MAA utilizing sulfuric acid, and the HIBAM, SIBAM, MAM, and MAA were fed to the thermal conversion apparatus. Samples were removed after the hydrolysis reaction and after the cracker reactor. The analysis for yield after the hydrolysis reaction and the cracker reactor as performed by nuclear magnetic resonance (NMR). The NMR results and the overall yield loss are shown in Table 1.

TABLE 1

| Example | Yield | | |
|---|---|---|---|
| | Hydrolysis | Thermal Conversion | Overall Loss |
| 1 | 95.71 | 91.91 | 3.80 |
| 2 | 96.32 | 92.62 | 3.70 |
| 3 | 96.82 | 92.73 | 4.09 |
| 4 | 97.40 | 91.31 | 6.09 |
| 5 | 97.88 | 91.27 | 6.61 |
| 6 | 97.23 | 92.46 | 4.77 |
| 7 | 97.43 | 91.54 | 5.89 |
| 8 | 97.22 | 93.35 | 3.87 |
| 9 | 98.00 | 92.46 | 5.54 |
| 10 | 97.00 | 91.73 | 5.27 |

An additional fifteen Comparative examples were run. The average overall loss for a total of 25 Comparative examples was 5.22% +/−0.26% with 95% confidence. The MAM was then esterified with methanol and phase separated into organic and aqueous phases, and then the organic layer was distilled yielding pure MMA.

For Examples 11–20, the process of the invention was run utilizing the plug flow thermal conversion apparatus of FIG. 2. ACH was hydrolyzed to HIBAM, SIBAM, MAM, and MAA utilizing sulfuric acid, and the HIBAM, SIBAM and MAA were fed to the thermal conversion apparatus. Samples were removed after the hydrolysis reaction and after the cracker reactor. The analysis for yield after the hydrolysis reaction and the cracker reactor was performed by nuclear magnetic resonance (NMR). The NMR results and the overall yield loss are shown in Table 2.

TABLE 2

| Example | Yield | | |
|---|---|---|---|
| | Hydrolysis | Thermal Conversion | Overall Loss |
| 11 | 95.73 | 92.06 | 3.67 |
| 12 | 96.28 | 92.82 | 3.46 |
| 13 | 96.10 | 92.10 | 4.00 |
| 14 | 96.97 | 93.60 | 3.37 |
| 15 | 97.86 | 92.54 | 5.32 |
| 16 | 96.70 | 93.98 | 2.72 |
| 17 | 99.00 | 92.45 | 6.55 |
| 18 | 98.55 | 94.49 | 4.06 |
| 19 | 97.88 | 93.84 | 4.04 |
| 20 | 98.16 | 93.67 | 4.49 |

An additional fifteen examples were run. The average overall yield loss for a total of 25 examples was 4.57% +/−0.28% with 95% confidence. The MAM was then esterified with methanol and phase separated into organic and aqueous phases, and then the organic layer was distilled yielding pure MMA.

The results above show that by utilizing the plug flow thermal conversion apparatus of the invention in the process of the invention, the overall yield was increased by 0.65% +/−0.38% with 95% confidence. A typical plant may produce in excess of 100 million pounds of MMA or MAA annually. Based on this production rate, the increased yield from the process of this invention could result in the plant having an increase in product of 650,000 pounds per year.

What is claimed:

1. A process for preparing methyl methacrylate, comprising:
   (A) hydrolyzing acetone cyanohydrin to produce a hydrolysis mixture comprising (α-hydroxyisobutyramide, α-sulfatoisobutyramide, 2-methacrylamide and methacrylic acid;
   (B) feeding said hydrolysis mixture to a cracker reactor, thermally converting said hydrolysis mixture in said cracker reactor to a cracker reactor mixture comprising 2-methacrylamide and methacrylic acid, said cracker reactor being operated under plug flow with the necessary retention time to produce said cracker reactor mixture, withdrawing said cracker reactor mixture from said cracker reactor;
   (C) reacting said cracker reactor mixture in at least one reactor with methanol to form a reaction mixture comprising methyl methacrylate.

2. The process of claim 1, further comprising a step (D) phase separating an organic stream comprising methyl methacrylate and methacrylic acid and an inorganic stream comprising sulfuric acid from the reaction mixture.

3. The process of claim 2, further comprising separating and purifying methyl methacrylate from the organic stream.

4. The process of claim 2, wherein an aqueous basic wash is added to the reaction mixture during separation step (D).

5. The process of claim 4, wherein a deemulsifier is also added to the reaction mixture during separation step (D).

6. The process of claim 5, wherein the deemulsifier is an acidic material.

7. A process according to claim 1 wherein the hydrolysis reaction is conducted in at least one hydrolysis reactor.

8. A process according to claim 1 wherein the hydrolysis reaction is conducted in three hydrolysis reactors.

9. A process for preparing methyl methacrylate, comprising:
   (A) hydrolyzing acetone cyanohydrin to produce a hydrolysis mixture comprising α-hydroxyisobutyramide, α-sulfatoisobutyramide, 2-methacrylamide and methacrylic acid;
   (B) providing a thermal conversion apparatus comprising at least one pipe with means for maintaining plug flow;
   (C) feeding said hydrolysis mixture to said thermal conversion apparatus, thermally converting said hydrolysis mixture in said thermal conversion apparatus to a cracker reactor mixture comprising 2-methacrylamide and methacrylic acid, said thermal conversion apparatus being operated under plug flow with the necessary retention time to produce said cracker reactor mixture, withdrawing said cracker reactor mixture from said cracker reactor;
   (D) reacting said cracker reactor mixture in at least one reactor with methanol to form a reaction mixture comprising methyl methacrylate.

10. The process of claim 9, wherein said at least one pipe is a straight length.

11. The process of claim 9, wherein said at least one pipe has at least one turn and the at least one turn has a Cheng Rotation Vane.

12. The process of claim 9, wherein plug flow is at least partially maintained by turns in the at least one pipe, said turns being smooth.

13. The process of claim 9, wherein plug flow is at least partially maintained by an expansion at the beginning of the thermal conversion apparatus, wherein said expansion is gradual so as to minimize back mixing of reactants entering the at least one pipe.

14. The process of claim 9, wherein plug flow is at least partially maintained by a constriction at the end of the thermal conversion apparatus, wherein said constriction is gradual so as to minimize back mixing of reactants and products exiting the at least one pipe.

15. The process of claim 9, wherein plug flow is at least partially maintained by selecting the diameter of the pipe.

* * * * *